United States Patent
Seifert et al.

(10) Patent No.: US 8,328,818 B1
(45) Date of Patent: Dec. 11, 2012

(54) DEVICES AND METHODS FOR TREATING BONE

(75) Inventors: Jody L. Seifert, Birdsboro, PA (US);
Paul W. Millhouse, Wayne, PA (US);
Jamie Calverley, Drexel Hill, PA (US);
Michael Lee Boyer, II, Phoenixville, PA (US); Nirali Patel, Bristol, PA (US);
David W. Ankney, Devon, PA (US);
Mark Adams, Honey Brook, PA (US)

(73) Assignee: Globus Medical, Inc., Audubon, PA (US)

( * ) Notice: Subject to any disclaimer, the term of this patent is extended or adjusted under 35 U.S.C. 154(b) by 852 days.

(21) Appl. No.: 12/201,112

(22) Filed: Aug. 29, 2008

Related U.S. Application Data

(60) Provisional application No. 60/969,241, filed on Aug. 31, 2007.

(51) Int. Cl.
*A61B 17/58* (2006.01)
*A61M 29/00* (2006.01)
(52) U.S. Cl. .................... 606/105; 623/17.12
(58) Field of Classification Search .......... 606/246–279, 606/60, 86 A, 90; 623/17.11–17.16
See application file for complete search history.

(56) References Cited

U.S. PATENT DOCUMENTS

| | | | | |
|---|---|---|---|---|
| 6,280,456 | B1 * | 8/2001 | Scribner et al. | 606/192 |
| 7,087,082 | B2 * | 8/2006 | Paul et al. | 623/17.11 |
| 7,473,277 | B2 * | 1/2009 | Boyer et al. | 623/17.15 |
| 7,972,382 | B2 * | 7/2011 | Foley et al. | 623/17.12 |
| 2004/0102774 | A1 * | 5/2004 | Trieu | 606/61 |
| 2005/0192671 | A1 * | 9/2005 | Bao et al. | 623/17.14 |
| 2007/0050032 | A1 * | 3/2007 | Gittings et al. | 623/17.12 |
| 2007/0088439 | A1 * | 4/2007 | Thramann | 623/17.13 |

* cited by examiner

*Primary Examiner* — Kevin T Truong
*Assistant Examiner* — Christopher Beccia

(57) ABSTRACT

A device is disclosed for reducing a vertebral compression fracture, comprising a superior end plate and an inferior end plate disposed along a vertical axis. The superior end plate and the inferior end plate are slidably separable in a vertical direction along the vertical axis. An interior chamber is provided in fluid communication with a port extending from an exterior to the interior chamber. The device is deployable within a vertebral body and expandable within the vertebral body by injecting a flowable material into the interior chamber thereby displacing the superior and inferior end plates along the vertical axis.

11 Claims, 11 Drawing Sheets

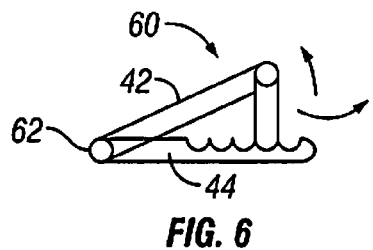
FIG. 6
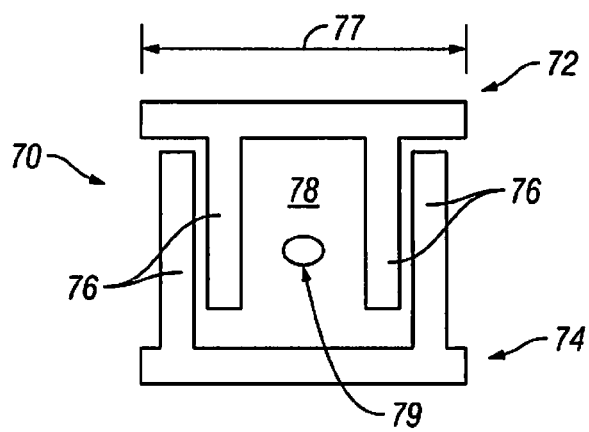
FIG. 7
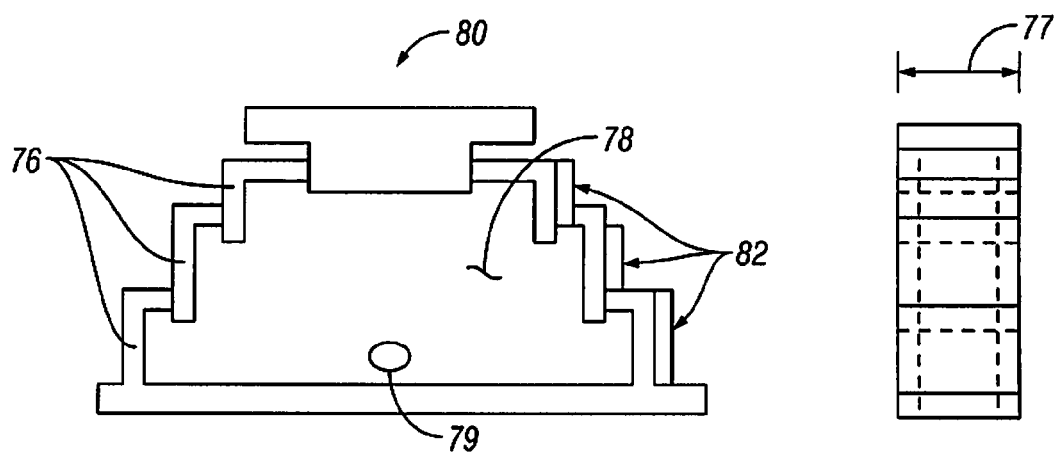
FIG. 8A
FIG. 8B

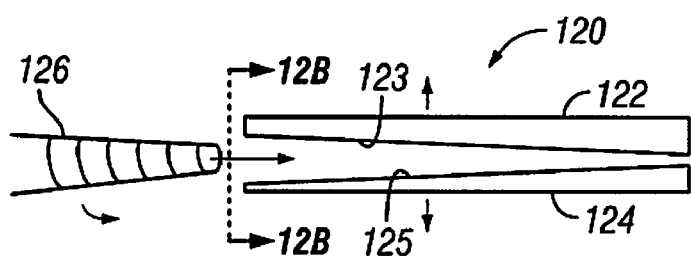
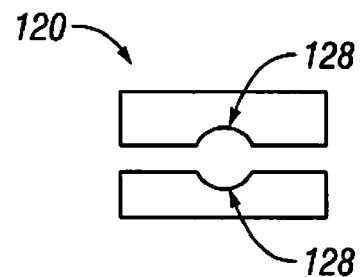
FIG. 12A     FIG. 12B
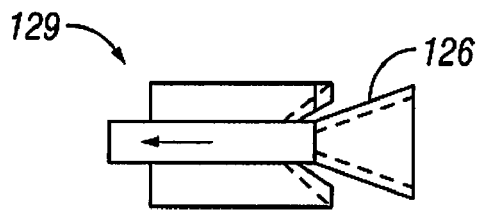
FIG. 12C
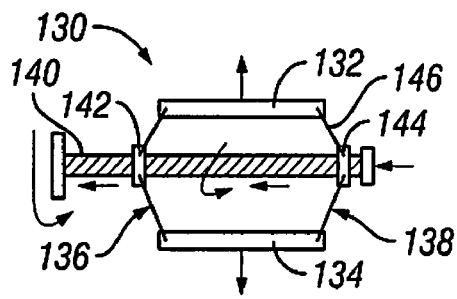
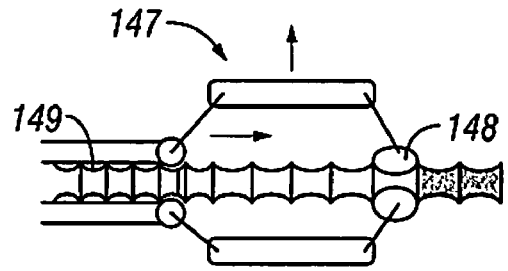
FIG. 13A     FIG. 13B
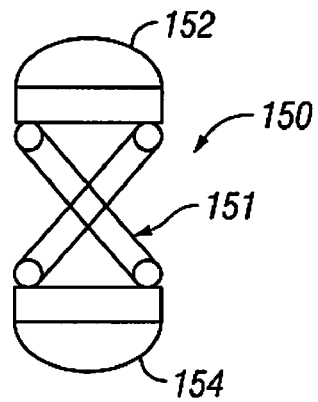
FIG. 14

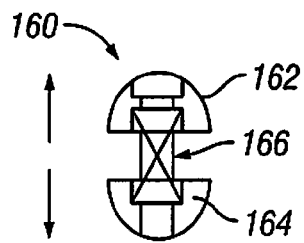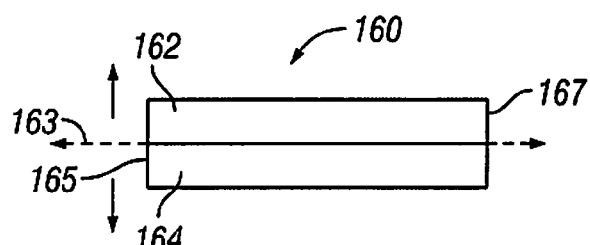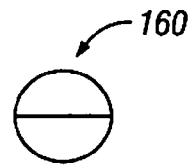
FIG. 15C  FIG. 15A
FIG. 15B
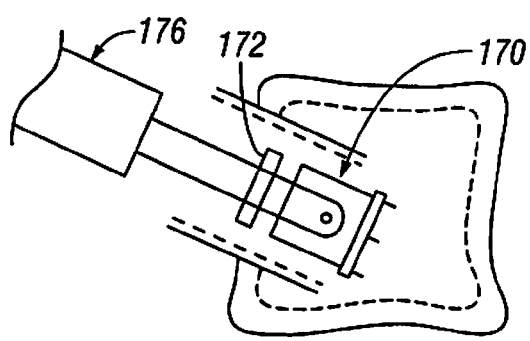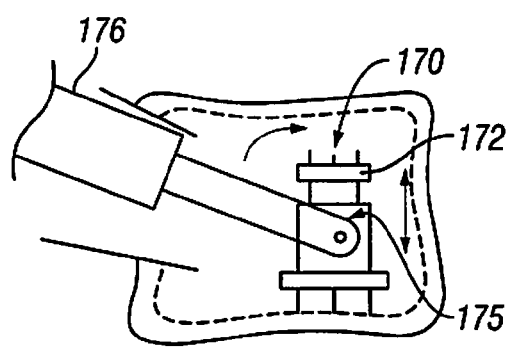
FIG. 16A  FIG. 16B

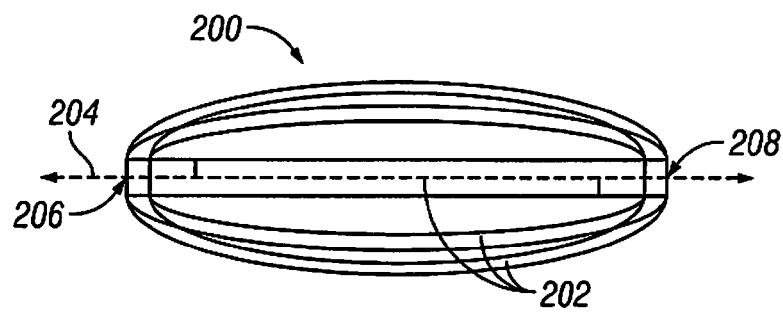
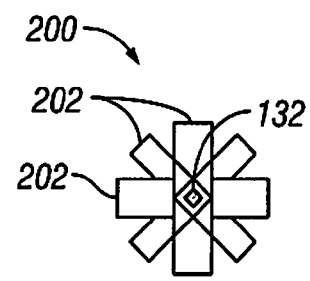
FIG. 19A  FIG. 19B
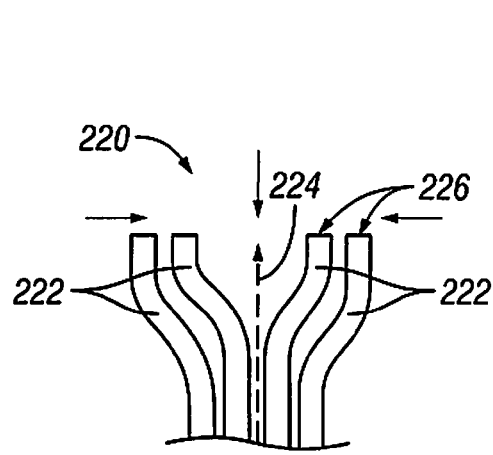
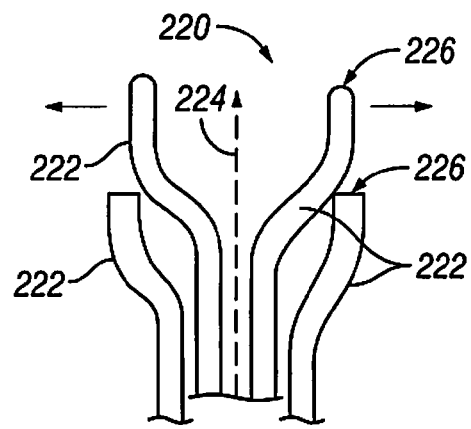
FIG. 20A  FIG. 20B

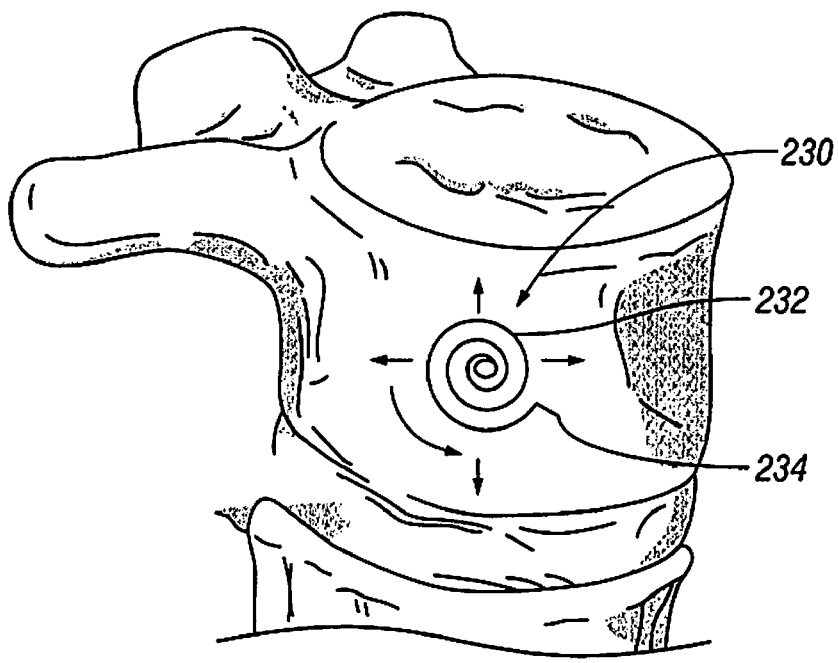
FIG. 21
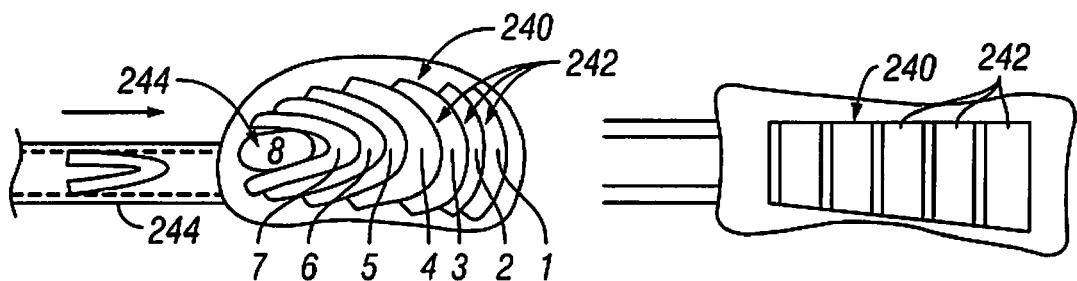
FIG. 22A  FIG. 22B

DEVICES AND METHODS FOR TREATING BONE

CROSS-REFERENCE TO RELATED APPLICATIONS

This application claims priority to U.S. Provisional Application Ser. No. 60/969,241 filed on Aug. 31, 2007, which is incorporated herein by reference in its entirety.

FIELD OF THE INVENTION

The present invention generally relates to devices and methods for treating bone. In particular, certain embodiments are directed to minimally invasive distraction and support devices and devices and methods to treat bone fractures.

BACKGROUND OF THE INVENTION

A minimally invasive distraction and support device and method would have significant application in orthopaedic surgical procedures, including acute and elective procedures to treat bone fractures and degenerative changes of the skeletal system and including vertebral compression fractures, interbody fusion, vertebral disc augmentation or replacement, and other compression fractures and/or non-orthopaedic surgical procedures.

A vertebral compression fracture is a crushing injury to one or more vertebrae. Vertebral fractures are generally associated with osteoporosis (the "brittle bone" disease), metastasis, and/or trauma. Osteoporosis reduces bone density, thereby weakening bones and predisposing them to fracture.

The osteoporosis-weakened bones can collapse during normal activity. In severe cases of osteoporosis, actions as simple as bending forward can be enough to cause a vertebral compression fracture. Vertebral compression fractures are generally known to be the most common type of osteoporotic fractures. The mechanism of these fractures is one of flexion with axial compression where even minor events may cause damage to the weak bone. While the fractures may heal without intervention, the crushed bone may fail to heal adequately. Moreover, if the bones are allowed to heal on their own, the spine will be deformed to the extent the vertebrae were compressed by the fracture. Spinal deformity may lead to breathing and gastrointestinal complications, and adverse loading of adjacent vertebrae.

Vertebral fractures happen mast frequently at the thoracolumbar junction, with a relatively normal distribution of fractures around this point. Vertebral fractures can permanently alter the shape and strength of the spine. Commonly, they cause loss of height and a humped back. This disorder (called kyphosis or "dowager's hump") is an exaggeration of the spinal curve that causes the shoulders to slump forward and the top of the back to look enlarged and humped. In severe cases, the body's center of mass is moved further away from the spine resulting in increased bending moment on the spine and increased loading of individual vertebrae.

Another contributing factor to vertebral fractures is metastatic disease. When cancer cells spread to the spine, the cancer may cause destruction of part of the vertebra, weakening and predisposing the bone to fracture.

Osteoporosis and metastatic disease are common root causes leading to vertebral fractures, but trauma to healthy vertebrae also causes minor to severe fractures. Such trauma may result from a fall, a forceful jump, a car accident, or any event that stresses the spine past its breaking point. The resulting fractures typically are compression fractures or burst fractures.

Vertebral fractures can occur without pain. However, they often cause a severe "band-like" pain that radiates from the spine around both sides of the body. It is commonly believed that the source of acute pain in compression fractures is the result of instability at the fracture site, allowing motion that irritates nerves in and around the vertebrae.

Various instruments and methods for the treatment of compression-type bone fractures and other osteoporotic and/or non-osteoporotic conditions have been developed. Such methods generally include a series of steps performed by a surgeon to correct and stabilize the compression fracture. A cavity is typically formed in the bone to be treated, followed by the insertion of one or more inflatable balloon-likes device into the bone cavity. Inflation of the balloon-like device causes a compaction of the cancellous bone and/or bone marrow against the inner cortical wall of the bone, thereby resulting in enlargement of the bone cavity and/or reduction of the compression fracture. The balloon-like device is then deflated and removed from the bone cavity. A biocompatible filling material, such as methylmethacrylate cement or a synthetic bone substitute, is sometimes delivered into the bone cavity and allowed to set to a hardened condition to provide internal structural support to the bone. In theory, inflation of the balloons restores vertebral height. However, it is difficult to consistently attain meaningful height restoration. It appears the inconsistent results are due, in part, to the manner in which the balloon expands in a compressible media and the structural orientation of the trabecular bone within the vertebra.

For example, it has been found that expansion of the balloon-like device can be difficult to control. Instead, when such a balloon-like device is inflated, expansion occurs along a path of least resistance. As a result, the direction of compaction of the cancellous bone and/or reduction of the compression fracture is not controllable, and expansion occurs in multiple directions and along multiple axes.

BRIEF DESCRIPTION OF THE DRAWINGS

FIG. 6 is a side view of another embodiment of a bone treatment device according to the invention;

FIG. 7 is an end view of another embodiment of a bone treatment device according to the invention;

FIGS. 8A-B are side and end views, respectively, of another embodiment of a bone treatment device according to the invention;

FIGS. 12A-C are side and end views of another embodiment of a bone treatment device according to the invention;

FIGS. 13-14 are side views of alternate embodiments of bone treatment devices according to the invention;

FIGS. 15A-C are side and end views of another embodiment of a bone treatment device according to the invention;

FIGS. 16A-B are side views of another embodiment of a bone treatment device shown in first and second positions with respect to a vertebral body;

FIGS. 19A-B are side and end views, respectively, of another embodiment of a bone treatment device;

FIGS. 20A-B are side views of another embodiment of a bone treatment device according to the invention;

FIG. 21 is a perspective view of another embodiment of a bone treatment device according to the invention shown in relation to a vertebral body;

FIGS. 22A-B are side and top views, respectively, of another embodiment of a bone treatment device according to the invention;

DETAILED DESCRIPTION OF THE ILLUSTRATED EMBODIMENTS

Embodiments of the present invention are generally directed to devices and methods for creating a cavity in bone. In particular, certain embodiments are directed to minimally invasive distraction and support devices and methods to treat bone fractures.

Figure 1:
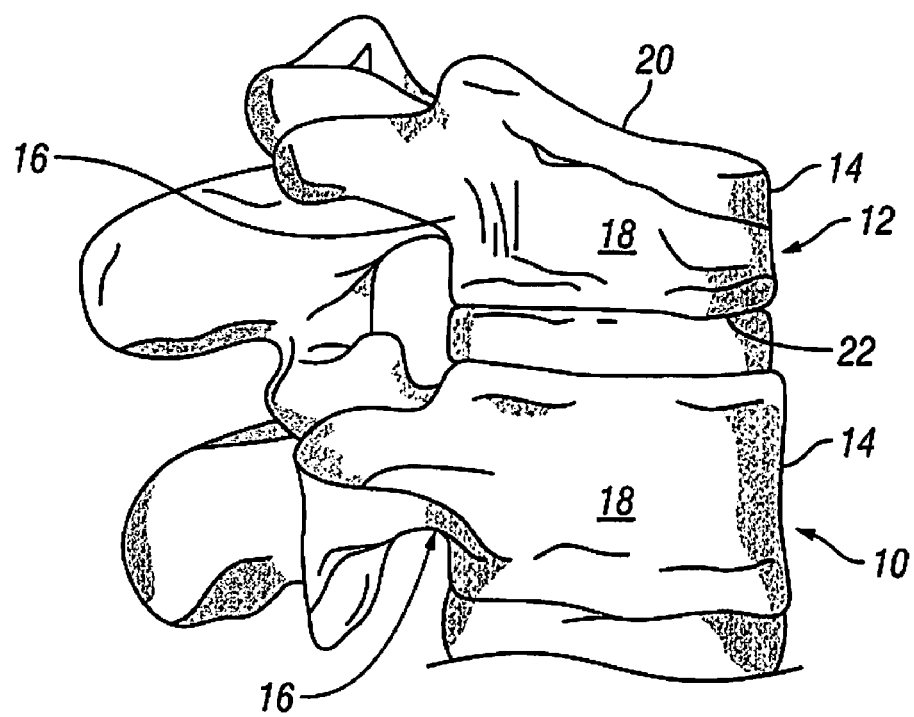
FIG. 1 shows a vertebral body having a compression fracture displacing its superior and anterior edge.
Figure 2:
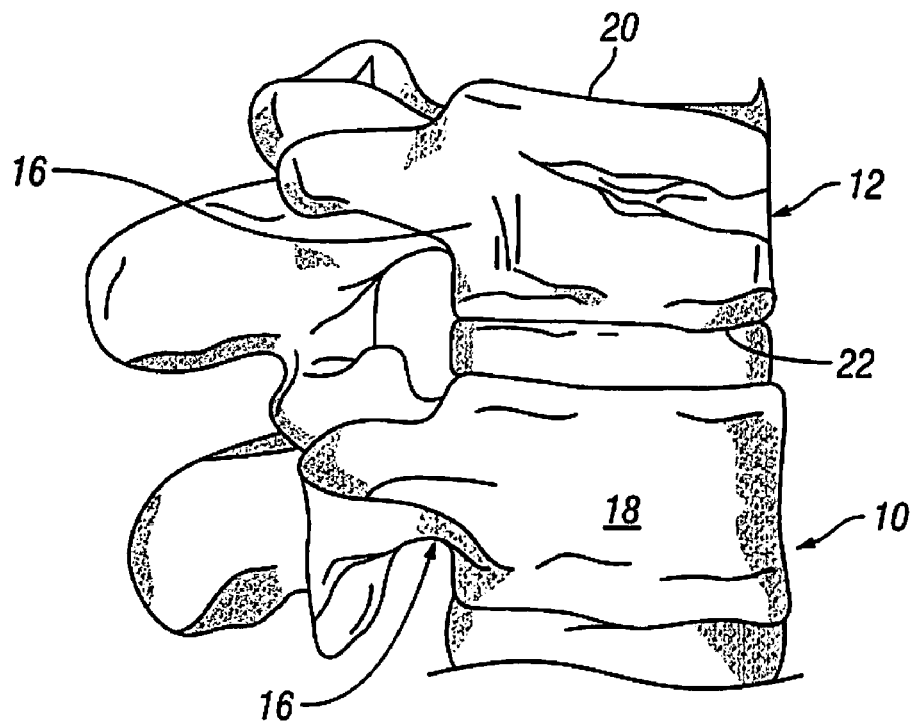
FIG. 2 shows a vertebral body, following treatment of a compression fracture.

The devices and methods are generally described by its application to the vertebral compression fracture. FIG. 1 illustrates two vertebrae 10, 12, each with an anterior side 14, a posterior side 16, and lateral sides 18 (only one shown). Vertebra 10 is fully intact, while vertebra 12 has a vertebral compression fracture (i.e. the top 20 and bottom 22 of the vertebra have been displaced towards each other). Referring to FIG. 2, the vertebral compression fracture of vertebra 12 is shown in a reduced or height restored state (i.e. the top 20 and bottom 22 of the vertebra 12 are distracted or displaced back to or near their original/intact positions). It is known that the force required to reduce the vertebral compression fracture can often be rather high.

Figure 3:
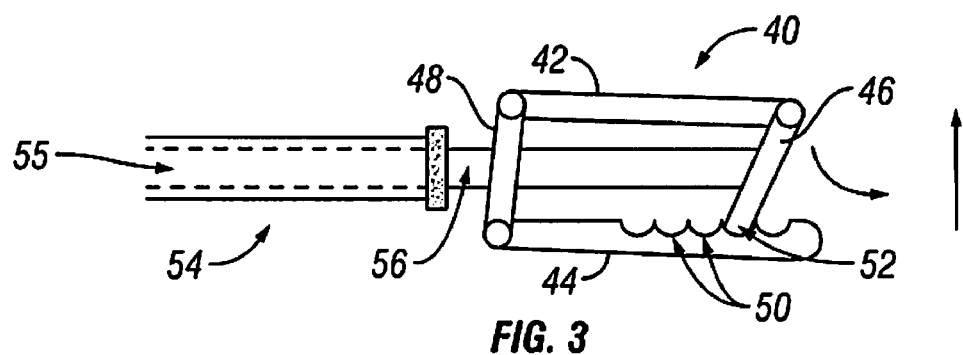
FIG. 3 is a side view of one embodiment of a bone treatment device according to the invention.
Figure 4:
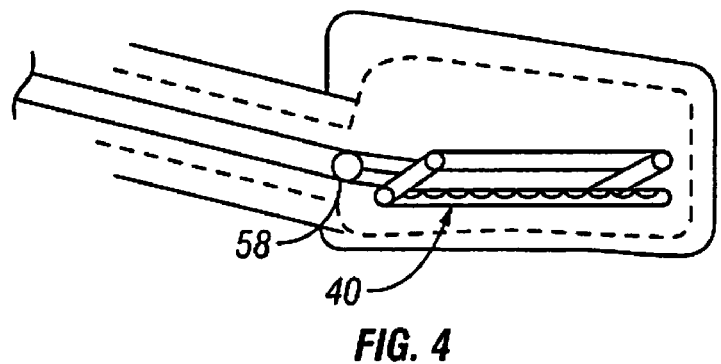
FIG. 4 is a side view of the device of FIG. 3 shown in a collapsed position.
Figure 5:
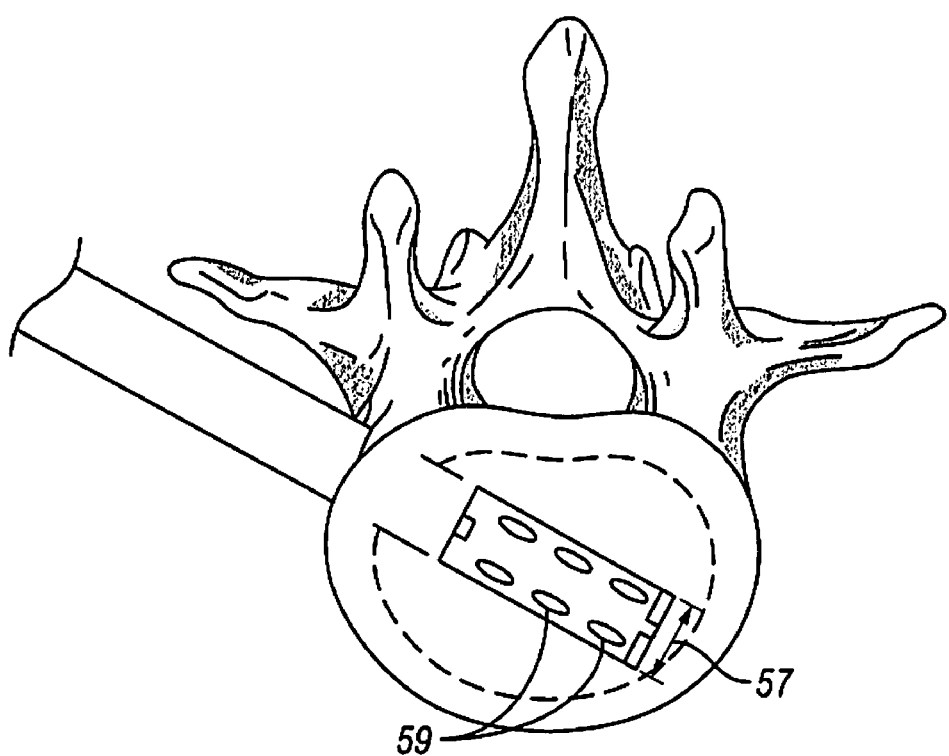
FIG. 5 is a top view of the device of FIG. 3 shown in an implanted position within a vertebral body.

Referring to FIGS. 3-5, one embodiment of a bone fracture distraction device or implant 40 is shown. Device 40 generally comprises a pair of rigid upper and lower plate members 42, 44 and an anterior end plate member 46 rotatably and linkedly connected to one of the upper or lower plate members 42, 44. In one variation, anterior plate member 46 is generally connected to the distal end of upper plate 42. A posterior end plate 48 may be linkedly connected between both the upper and lower plates 42, 44 adjacent the posterior end of plates 42, 44. In general, anterior plate 46 may swing or rotate about the distal end of plate 42. Plates 42, 44, 46, and 48 may be generally thin wafer like plate members and may have varying widths and lengths. As best seen in the top view shown in FIG. 5, in one embodiment, the size of the plates could have a width 57 between about 3 mm and about 4 mm wide. Also shown in FIG. 5, according to one aspect, the upper and lower plate members 42, 44 may define openings or perforations 59 to facilitate passage or bone cement and/or bone growth therethrough.

A plurality of ratcheting grooves 50 may be provided along a portion of the interior of lower plate 44 to ratchetedly engage the free end 52 of anterior plate 46. In this regard, as the anterior plate 46 is moved or rotated outwards, the free end 52 of anterior plate 46 slidingly engages the grooves 50 similar to a ratchet mechanism such that when a downward force is applied to upper plate 42, anterior end plate 46 may only move in an outward direction and the ratchet grooves 50 prevent movement of free end 52 in an opposite inward direction. Such a ratchet feature facilitates distraction and support of a bone fracture as the anterior end plate 46 is rotated or pushed outward. In the exemplary embodiment depicted in FIG. 3, end plate 46 is linkedly attached to upper plate 42, however, end plate 46 could alternatively be linkedly connected to lower plate 44 and a similar ratchet like interface may be provided on the upper plate.

As is illustrated in FIG. 4, the device 40 may be positioned in a collapsed state with the upper plate 42, lower plate 44, and anterior and posterior plates 46, 48 folded generally flat with the free end 52 of anterior plate 46 positioned adjacent the posterior end of device 40. In this regard, in a collapsed state device 40 is a generally thin member and may be introduced through smaller channels within the vertebra. The device may be deployed or expanded within the vertebra by displacing or pushing the anterior end plate 46 in an outward direction and creating a vertical force that displaces upper and lower plates 42, 44 away from each other to thereby reduce a vertebral compression fracture. Ratchet grooves 50 prevent movement of free end 52 of anterior plate 46 in an opposite inward direction and further facilitates distraction and support of a bone fracture as the anterior end plate 46 is rotated or pushed outward. As shown in FIG. 3, in an expanded state, device 40 generally resembles a box or parallelogram. In one embodiment, an insertion tool 54 may be removably attached to a posterior portion of device 40 and a pusher rod 56 or similar device may be advanced in an anterior direction 55 to push or force anterior end plate 46 outward in the anterior direction. In another variation, a flexible joint or linkage may be provided adjacent the posterior portion of device 40 to facilitate insertion and advancement of pusher rod 56. According to one aspect of this embodiment, a portal or opening 58 may be provided through posterior plate 48 to facilitate attachment of insertion tool 54 and provide a passage though which bone cement or other filler material may be inserted into the interior of the device.

According to one embodiment of a method of treating bone according to the invention, a bone treatment device, such as device 40 described above, may be introduced into a damaged vertebral body by first making one or more fairly small incisions in the tissue of a patient. Following that, an opening may be formed in the vertebral body by means of well-known and frequently used instruments. In one variation an opening may be made via the pedicle which connects the rear part of the vertebra to the vertebral body and the bone treatment device or implant may be inserted into a vertebral body through a minimally invasive procedure such as through a small diameter portal.

For example, in the embodiment of FIGS. 3-5, device 40 may be inserted in a first or collapsed condition, as shown in FIG. 4, the instrument is pushed into the bone portion through the aforesaid opening (not shown) in its collapsed position by means of an auxiliary insertion tool 54 and placed into the vertebral cavity 18. Subsequently, the device 40 may be expanded within the vertebral cavity as described above until that expansion is complete and the bone treatment device may be fixated in the extended condition. In addition, the insertion tool 54 may then be disconnected from the device. If the surgeon should decide just before the fixation stage that the implant is not correctly positioned in the vertebral cavity, he may collapse the device again and withdraw it through the aforesaid openings.

In the extended or expanded position, the bone treatment device 40 is generally configured and dimensioned to stretch the vertebra substantially to its original dimension, as it were. In the extended or expanded condition the inserted device or implant may take up loads that are exerted on the vertebra. The space formed within the vertebra may then be filled with a filler material or other therapeutic material which may stimulate bone growth as described above.

Referring to FIG. 6, another embodiment of a bone fracture distraction device 60 is shown. Device 60 is generally similar to device 40 described above except the posterior plate is removed and the upper and lower plates 42, 44 are directly hingedly or linkedly attached at a posterior end 67. In operation, device 60 may be ratchetedly advanced similar to device 40 described above, however, in an expanded stated device 60 resembles a triangle. According to one embodiment, bone growth media and/or bone cement may be inserted or injected into device 40 to permanently lock into place or allow bone to grow through implant.

The materials used in constructing devices 40, 60, and the other devices described below may comprise any of a wide variety of biocompatible materials. In certain embodiments, a radiopaque material, such as metal (e.g., stainless steel, titanium alloys, or cobalt alloys) or a polymer (e.g., ultra high molecular weight polyethylene) may be used, as is well know in the art. In alternate embodiments, a radiolucent material, such as polyetheretherketone (PEEK) may be used. Polymethylmethacrylate (PMMA) can also be used. In other alternate embodiments, a generally porous or microsphere material may be used. Exemplary microsphere material that may be used is disclosed in U.S. patent application Ser. No. 11/552,244, filed Oct. 24, 2006 and entitled "Porous and Nonporous Materials for Tissue Grafting and Repair," the entire contents of which are incorporated herein by reference.

Referring to FIG. 7, an end view of another embodiment of a bone treatment device 70 is shown. Device 70 generally comprises a superior end plate 72 and an inferior end plate 74 telescopingly interconnected such that end plate 72 and end plate 74 may slide apart or separate in the vertical direction. According to one aspect of this embodiment, arm extensions 76 may extend downward from superior plate 72 and upward from inferior plate 74 and arms 76 Extensions 76 may be juxtaposed side by side to permit sliding or telescoping contact therebetween and allow relative vertical movement while generally preventing lateral displacement. An interior chamber 78 may be defined interior to arms 76 and end plates 72, 74 and a port or opening 79 may be provided to allow access to the interior chamber from the exterior of device 70. In one variation, the device 70 may be deployed or expanded within the vertebra by injecting a filler material into the interior chamber to fill chamber 78 and creating a vertical force that displaces upper and lower plates 72, 74 away from each other to thereby reduce a vertebral compression fracture. The filler material may be liquid, semi-liquid, or any other flowable substance or injectable material. Some exemplary substances include, but are not limited to, bone cement such as PMMA, crushed bone, bone pieces, bone matrix, polymers, microsphere materials or combinations thereof. As depicted in the end view of FIG. 6, the lateral width 77 of device 70 may be between about 4 mm to about 6 mm. According to one embodiment, end plates 72, 74 may be curved or arcuate when viewed from the top, while in alternate embodiments, end plates 72, 74 may have a rectangular shape. However, in other embodiments, end plates 72, 74 may have any desired shape. In another variation, endplates 72, 74 may have convex or concave profiles when viewed from the side. In one embodiment, plates 72, 74 and extensions 76 may be made from resorbable polymer material. In another embodiment, device 70 may be made from a rigid biocompatible metal. In yet another embodiment, device 70 may be made from a PEEK material. In one variation, plates 72, 74 may have perforations extending therethrough to permit the filler to flow or exit therethrough and/or to permit bone to grow through to facilitate fusion.

Referring to FIGS. 8A-8B, another embodiment of a bone treatment device 80 is shown in an expanded or extended condition. Device 80 is similar to device 70 described above, except a plurality of telescoping or expandable vertical segments or regions 82 are provided. Each region 82 may comprise another set or pair of arm extensions 76 extending downward form a superior region and upward from an inferior region. Similar to device 70 described above, extensions 76 may be juxtaposed side by side to permit sliding or telescoping contact therebetween and allow relative vertical movement while generally prevent lateral displacement. Similar to device 70, an interior chamber 78 may be defined interior to arms 76 and end plates 72, 74 and the device may expand or telescope upward when interior chamber 78 is filled. In this embodiment, device 80 may generally expand or telescope upwards a greater distance than device 70 if both devices are provided with the same length extension arms 76. For example, in the embodiment of FIG. 7, device 80 may expand or telescope upwards a total of three times the initial height since there are three telescoping segments 82. In alternate embodiments, more than three vertical telescoping segments may be provided. In yet another embodiment, one or more lateral telescoping segments may be provided in addition to the vertical telescoping segments.

Figure 9:
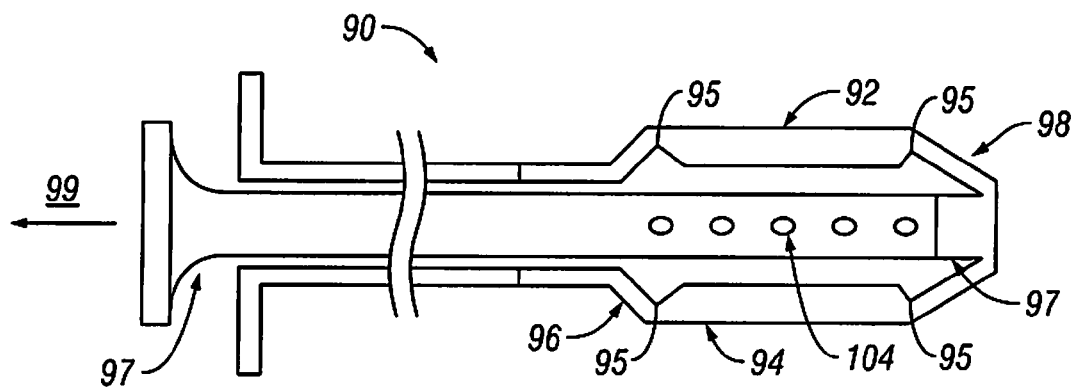
FIG. 9 is a side view of another embodiment of a bone treatment device according to the invention.
Figure 10:
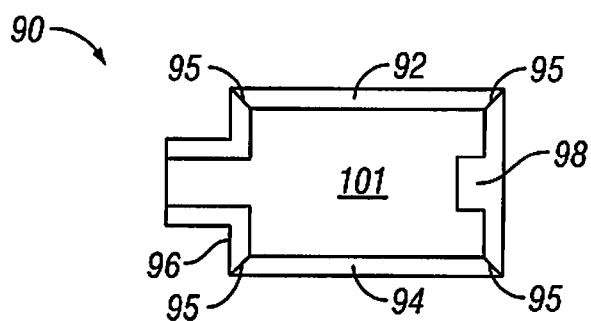
FIG. 10 is a top view of the device of FIG. 9 shown in an expanded condition.
Figure 11:
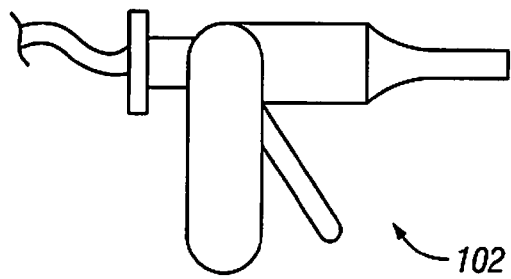
FIG. 11 is a side view of an installation gun useable with the device of FIG. 9.

Referring to FIGS. 9-11, an alternate embodiment of a bone treatment device 90 is shown. Bone treatment device 90 generally comprises a collapsible box-like frame member having upper and lower plates 92, 94 and posterior and anterior support legs 96, 98. According to one aspect of the embodiment, device 90 may be molded from a polymer material such as PEEK and may have thinwalled or weakened corner sections 95 such that device 90 may be collapsed or flattened. In this regard, device 90 may be inserted into a vertebral body in a collapsed condition as generally shown in FIG. 9 and a plunger 97 may be removably attached to an interior portion of a distal or anterior support leg 98. In one variation, the device 90 may be deployed or expanded within the vertebra by may be pulled backward in the direction of arrow 99 to force the box to come together, as shown in FIG. 10, and creating a vertical force that displaces upper and lower plates 92, 94 away from each other to thereby reduce a vertebral compression fracture. In one variation, device 90 may be molded such that it is biased to maintain its boxlike shape so that it in operation it snaps together. As shown in FIG. 10, in an expanded condition, device 90 defines an interior chamber 101. As described above with respect to previous embodiments, chamber 101 may be filled with a filler material such as bone cement or other similar material to facilitate bone growth and/or fusion. In this regard, plunger 97 may be provided with a plurality of perforations or holes 104 to deliver bone cement therethrough to chamber 101. Referring to FIG. 11, a gun or triggered device 102 may be attached to the proximal end of plunger 97 to deliver bone cement therethrough under pressure.

Referring to FIGS. 12A-B, another embodiment of a bone fracture treatment device 120 is shown. As seen in the side view of FIG. 12A, treatment device 120 generally comprises upper and lower rigid end plates 122, 124 configured and dimensioned to receive a threaded insert member 126 therebetween. In one variation, the threaded insert member 126 may have a generally tapered profile and may be similar to, for example, a pipe thread. In another variation, threaded insert 126 may have a generally straight profile. In one variation, the superior and inferior surfaces of plates 122, 124 may be maintained at least initially in a generally parallel relation. The interior sides or surfaces 123, 125 of plates 122, 124 may be tapered lengthwise with a wider initial separation between plates 122, 124 adjacent the posterior side of device 120 and a narrower separation adjacent an anterior side. As shown in the end view of FIG. 12B, plates 122, 124 may have opposed semi-circular shaped notches, grooves, or troughs 128 disposed along the interior portion thereof. In one variation, plates 122, 124 may be constrained laterally such that notches 128 remain generally vertically aligned. In certain embodiments, notches 128 may be threaded to receive the threaded insert member 126. The device may be deployed or expanded within the vertebra by inserting the threaded insert member 126 between end plates 122, 124. Because the interior of end plates 122, 124 is tapered, as the threaded insert member is inserted or threadedly advanced from the posterior end to the anterior end, device 120 may expand in the superior-inferior direction and create a vertical force that displaces upper and lower plates 122, 124 away from each other to thereby reduce a vertebral compression fracture. Referring to FIG. 12C, an alternate embodiment of a bone treatment device 129 may be provided that is generally similar to device 120 except device 129 may be expanded by drawing backward insert member 126 in the posterior direction.

Referring to FIG. 13A, another embodiment of a bone fracture treatment device 130 is shown. Device 130 generally comprises rigid superior and inferior plates 132, 134 interconnected by expandable posterior and anterior walls 136, 138. In this embodiment, a central expansion screw 140 may extend through nuts 142, 144 on opposite ends of device 130. Nuts 142, 144 may be rotatably connected to a central portion of walls 136, 138. In this regard, plates 136, 138 may comprise generally rigid bar members or linkages 146 that are rotatably connected to nuts 142, 144. The device may be deployed or expanded within the vertebra by rotating central expansion screw 140 to draw nuts 142, 144 together. When nuts 142, 144 are drawn together, superior and inferior plates 132, 134 may distract, separate apart, or expand in the superior-inferior direction and create a vertical force to thereby reduce a vertebral compression fracture. In an alternate embodiment, shown in FIG. 13B, an alternative device 147 may have a ratcheting ring 148 disposed over a serrated shaft 149 and device 147 may be expanded by linearly advancing shaft 149 with respect to rings 148.

Referring to FIG. 14, another bone treatment device 150 is shown. Device 150 is similar to device 130 described above, except a scissor jack-like mechanism 151 may be used to move the upper and lower plates 152, 154 apart and move device 150 to its expanded position.

Referring to FIGS. 15A-C, an alternate embodiment of a bone treatment device 160 is shown. Device 160 generally comprises a spring loaded assembly with an upper portion 162 and a lower portion 164. As shown in FIG. 15A, device 160 may have an elongate structure extending along a longitudinal axis 163 from a posterior end 165 to an anterior end 167. As shown in FIG. 15C one or more biasing members or compression springs 166 may be disposed between upper an lower portion 162, 164 to bias the upper and lower portions apart. In an alternate embodiment, one or more leaf springs may be disposed between upper and lower portions 162, 164. One or more flexible bands may be disposed on or around the exterior of device 160 to prevent the device from coming apart. As with previously described embodiment, device 160 may be inserted into a vertebral body through a minimally invasive procedure such as through a small diameter portal. Once device 160 exits the portal into the interior portion of the vertebral body, the upper and lower portions 162, 164 are biased apart and creating a vertical force that displaces upper and lower plates 162, 164 away from each other to thereby reduce a vertebral compression fracture.

Referring to FIGS. 16A-B, another embodiment of a bone treatment device 170 is shown. Device 170 generally comprises an upper support 172 and a lower support 174 threadably interconnected thereto. Device 170 may be threadably expanded by, for example, a gear mechanism 175 accessible on an exterior portion of device 170 and actuatable through an insertion tool 176. Exemplary threaded interconnection mechanisms, gear mechanisms, and actuation mechanism useable with device 170 is discussed in U.S. patent application Ser. Nos. 11/110,844 and 11/464,625, filed Apr. 21, 2005 and Aug. 15, 2006, respectively, and both entitled "Expandable Vertebral Prosthesis," the entire contents of which are incorporated herein by reference. As shown in FIG. 16A, device 170 may be pivoted after insertion into a vertebral body such that that device 170 may turn from an initial alignment along the pedicle to a more vertical orientation as shown in FIG. 16B.

Figure 17:
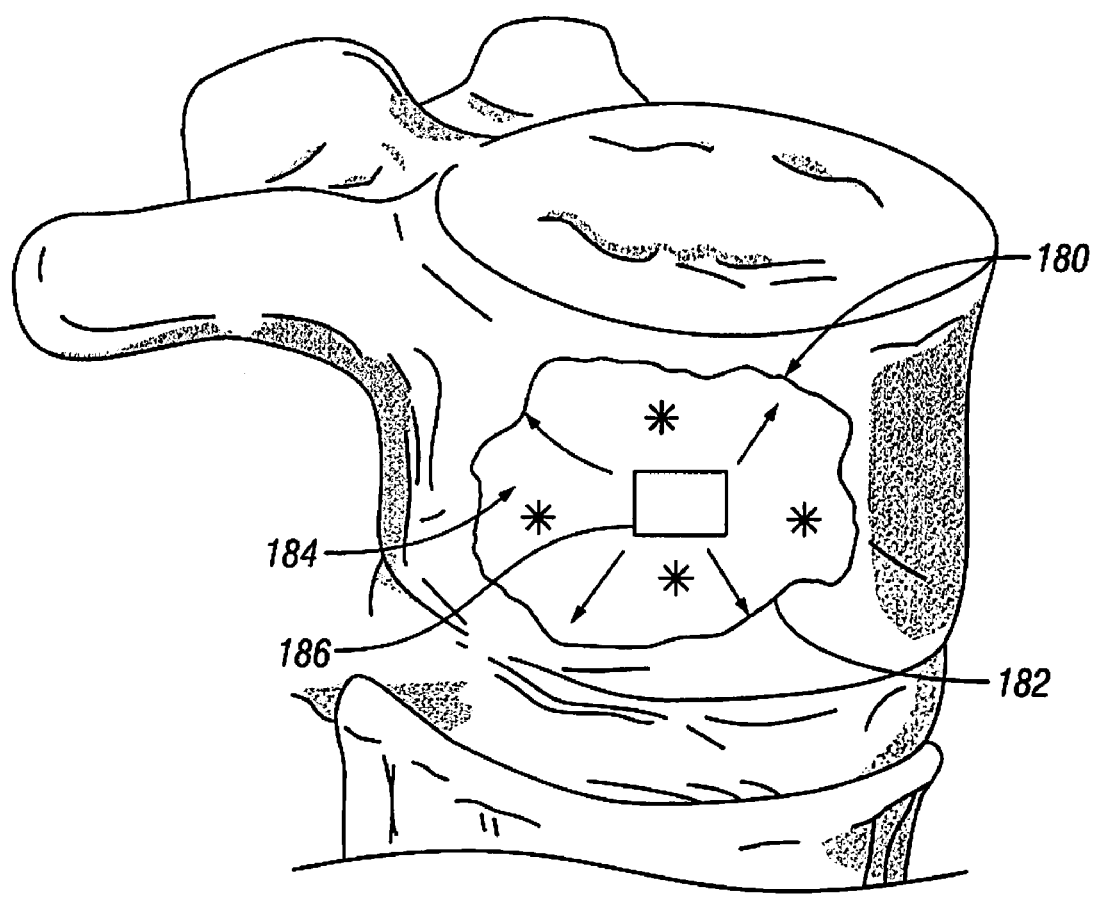
FIG. 17 is a perspective view of another embodiment of a bone treatment device according to the invention shown in relation to a vertebral body.

Referring to FIG. 17, another embodiment of a bone fracture treatment 180 device is shown. Device 180 generally comprises an outer wall membrane or sack 182 enclosing a central region 184. In one variation, outer wall membrane 182 is made from a generally flexible yet resilient material, including, but not limited to, cloth, mesh any or other flexible elastic plastic or synthetic material, such as polyurethane. Any biocompatible material may be used that has the ability to be inserted in a cannulated tube and inserted in the vertebral body. Once in the vertebral body, the material should be able to be filled with a material to stretch the material outward to cause distraction of the end plates. Wall membrane 182 may have one or more openings or perforations extending through the wall from the exterior to the central region 184. In one embodiment, an expandable sponge-like, absorbent, or memory foam member 186 may be positioned in the central region 184 and may be housed or enclosed by wall membrane 182. The device may be deployed or expanded within the vertebra by activating the foam member 186 to trigger expansion thereof to create a vertical or expansive force to thereby reduce a vertebral compression fracture. In one variation, the expansion of foam member 186 may be triggered by exposure to elevated temperatures or fluids such as, for example, water or body fluid. Such exposure may be assisted by injecting the fluid through the wall membrane 182 or through a predefined connection. In alternate embodiments, a hardening filler material such as bone cement may be injected into foam member 186 to trigger expansion and the cement may harden thereafter with foam member 186 in an expanded state. In certain embodiments, wall membrane 182 may be defined with a limited flexibility such that it may expand to enclose a maximum volume of the central region 184 and prevent overexpansion of foam member 186. In this regard, wall membrane 182 may be designed and configured to expand to conform to the interior volume of an intact healthy vertebral body of a particular patient as desired or diagnosed by a practitioner user.

Figure 18:
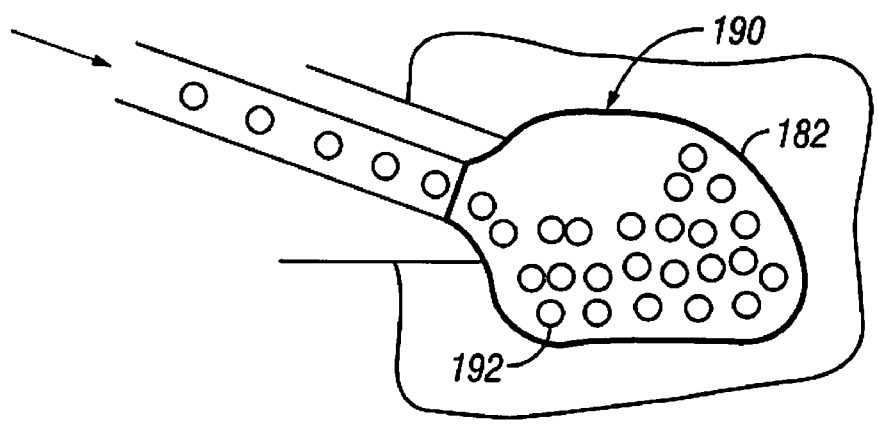
FIG. 18 is a perspective view of another embodiment of a bone treatment device according to the invention.

Referring to FIG. 18, another embodiment of a bone treatment device 190 is shown. Device 190 is similar to device 180 described above, except the membrane 182 may be filled with a porous filler material 192 such as a microsphere material. Exemplary microsphere material that may be used with device 190 is disclosed in U.S. patent application Ser. No. 11/552,244, filed Oct. 24, 2006 and entitled "Porous and Nonporous Materials for Tissue Grafting and Repair," the entire contents of which are incorporated herein by reference. The device may be deployed or expanded within the vertebra by inserting or injecting a plurality of microsphere members to trigger expansion of device 190 to create a vertical or expansive force to thereby reduce a vertebral compression fracture.

Referring to FIGS. 19A-B, another embodiment of a bone fracture treatment 200 device is shown. Device 200 generally comprises a plurality of elongate bands or strips 202 having a generally arcuate shape extending along a longitudinal axis 204 from a posterior end 206 to and anterior end 208. Bands 202 are pinned or fixed together at the posterior and anterior ends 206, 208 and are generally spaced radially about axis 204. According to one embodiment, device 200 may alter its shape from, for example, a collapsed elongate tubular structure having a first diameter or maximum height measured transverse to axis 204 to a general ovoid shaped or partially spherical shaped scaffold having a second larger diameter or maximum height measured transverse to axis 204. In one variation, bands 202 may be made from a generally flexible yet resilient material, including, but not limited to, nitinol, titanium, stainless steel, PEEK, any or other flexible biocompatible material. It could also be made from memory alloy that resumes a predefined shape when exposed to heat or other triggering methods. In one variation device 200 may have a central rod 132 to facilitate insertion and expansion thereof in-situ.

Referring to FIGS. 20A-B, cross-sectional views of another embodiment of a bone treatment device 220 is shown. Device 220 generally comprises a plurality of elongate finger members 222 extending along a central longitudinal axis 224. In one variation, fingers 222 may be made from a generally flexible yet resilient material, including, but not limited to, nitinol, titanium, stainless steel, PEEK, any or other flexible biocompatible material. Fingers 222 could also be made from memory alloy that resumes a predefined shape when exposed to heat or other triggering methods. The free ends 226 of fingers 222 may be biased outward such that when fingers 222 are pushed outward beyond the end of a tubular portal free ends 226 flare or expand outward. In this regard, as shown in FIG. 20B, the distal ends 226 of the fingers 222 may extend laterally beyond the wall of the portal tube or delivery cannula and may be used to create a cavity within the vertebral body. In one variation, the device 220 may be deployed or expanded within the vertebra when pushed beyond the end of the working cannula to create a vertical force to reduce a vertebral compression fracture. In certain embodiments, there may be a plurality of fingers 222 radially disposed about axis 224. In one embodiment, at least four fingers are provided. In another embodiment, the fingers may be semi-tubular and each finger 222 may comprise one fourth of a portion of a cylinder.

Referring to FIG. 21, another embodiment of a bone treatment device 230 is shown. Device 230 generally comprises a coil spring body 232. In one variation, spring body 232 may be made from a generally flexible yet resilient material, including, but not limited to, nitinol, titanium, stainless steel, PEEK, any or other flexible biocompatible material. Spring body 232 could also be made from memory alloy that resumes a predefined shape when exposed to heat or other triggering mechanisms. In one embodiment, a foot or tab 234 may extend from one end of body 232 to grip, engage, catch onto or otherwise contact a bone portion of a vertebral body, such as an end plate. Spring body 232 may be configured and dimensioned to be biased outward. In one variation, the device 230 may be deployed or expanded within the vertebra by rotating or uncoiling the spring to create a vertical force to thereby reduce a vertebral compression fracture. Similar to many of the embodiments described above, device 230 may be inserted in a minimally invasive procedure into the vertebral body such as, for example, through a working cannula extending through the pedicle. In one variation, spring body 232 may be any kind of coiled band. In one variation, spring 232 could be a flat spring that coils out like a rolled up sheet of paper. In one variation, the inner part or central portion of spring body 232 may include a one way ratchet mechanism which would allow expansion and prevent contraction of spring body 232.

Referring to FIGS. 22A-B, another embodiment of a bone treatment device 240 is shown. Device 240 generally comprises a plurality of plates or folded plates or folded bands 242. In one variation, bands 242 may be made from a generally flexible yet resilient material, including, but not limited to, nitinol, titanium, stainless steel, PEEK, any or other flexible biocompatible material. Plates 242 could also be made from memory alloy that resumes a predefined shape when exposed to heat or other triggering methods. Bands 242 may be forcibly advanced into an interior of a vertebral body through a minimally invasive technique such as through a working cannula as shown in FIG. 22A and packed into the interior of a vertebral body from the anterior portion to the posterior portion. As best seen in FIG. 22A, bands 242 may be thin wafer like members that are flexible enough to be folded or curved to fit down a cannula, yet resilient enough to reform or spring back to a more straightened shape once inserted into the vertebral body. Once a desired amount of bands 242 are inserted into the vertebral body a final or posterior most piece 244 may be inserted into the vertebral body. In one variation, piece 244 has a general wedge shape to facilitate the packing of bands 242 within the vertebral body and transfer lateral force the bands to trigger cause the bands to expand in a vertical direction and create a vertical or expansive force to thereby reduce a vertebral compression fracture. Wedge piece 244 may also function to lock the bands in place or keep the assembly together. As with previous embodiments, device 240 may be used in a minimally invasive procedure and in one embodiment bands 242 may be fed down a tube or portal 244, as shown in FIG. 22A. In one variation bands 242 may be fed along a guidewire so the bands 242 may have a central hole to accommodate the guidewire.

Figure 23A:
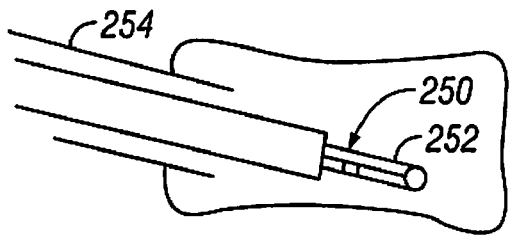
FIGS. 23A-B are side perspective views of one embodiment of a cavity creation device according to the invention.
Figure 23B:
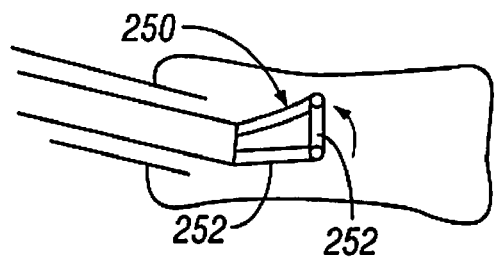

Referring to FIGS. 23A-B, an embodiment of a cavity creation tool 250 is shown. Cavity tool 250 generally comprises a plurality of bars or legs 252 rotatably interlinked. According to one variation, at least three bars 252 may be interlinked. In operation, device 250 may inserted through a cannula 254 into a vertebral body with legs 252 in a collapsed condition and once inserted into the vertebral body the legs 252 may be manipulated to expand outward and rotated an moved about within the vertebral body to excavate or break up the cancellous bone within the vertebral body.

Figure 24A:
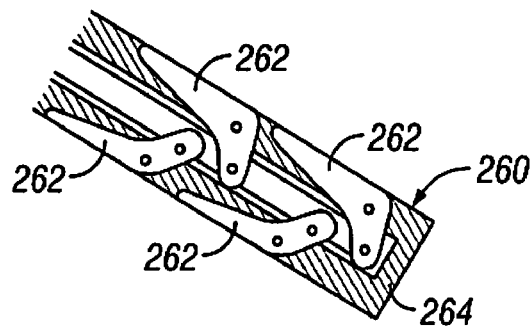
FIGS. 24A-B are views of another embodiment of a cavity creation device according to the invention.
Figure 24B:
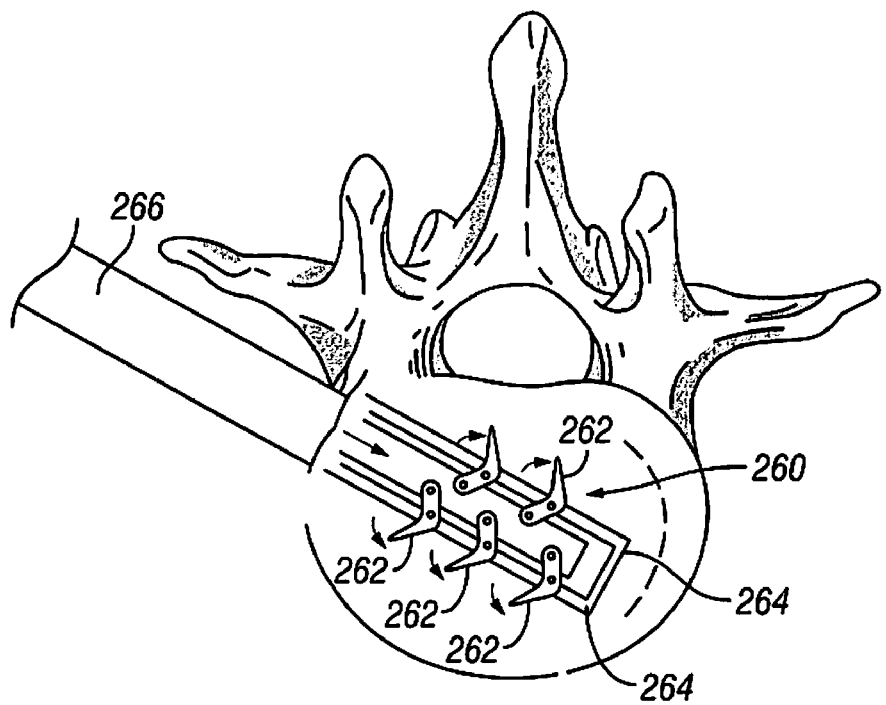
Figure 25:
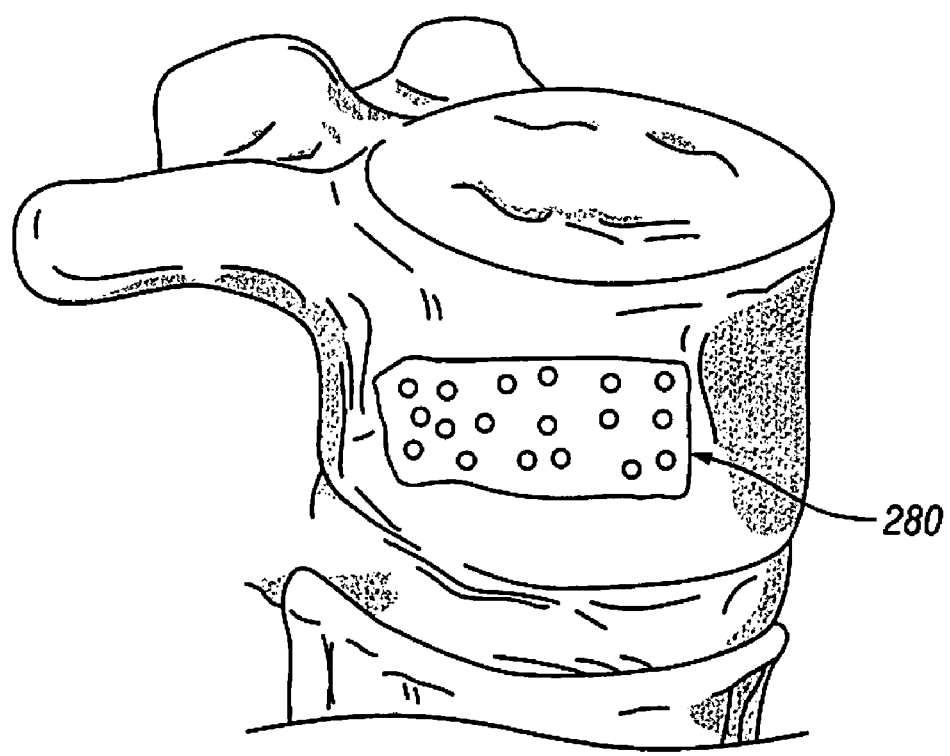
FIG. 25 is a perspective view of another embodiment of a bone treatment device according to the invention shown in relation to a vertebral body.

Referring to FIGS. 24A-B, another cavity creation tool 260 is shown. Tool 260 generally includes a plurality of L shaped fingers 262 rotatably connected to an exterior portion of a tubular member 264. Finger 262 may be moved from a retracted position, shown in FIG. 24A, to facilitate insertion of tool 260 through a working cannula 266 to an extended position, as shown in FIG. 24B, to facilitate excavation of cancellous bone from the interior of a vertebral body. Similar to tool 250 described above, tool 260 may be rotated and manipulated within the vertebral body to break up the interior cancellous bone of the vertebral body to, among other things, create a cavity to receive a bone treatment device. For example, referring to FIG. 25, another exemplary bone treatment device 280 that may be inserted into such a cavity is shown. Device 280 generally comprises a sponge or sponge-like member that may be filled with bone cement or bone matrix.

While it is apparent that the invention disclosed herein is well calculated to fulfill the objects stated above, it will be appreciated that numerous modifications and embodiments may be devised by those skilled in the art.

What is claimed is:

1. A device for reducing a vertebral compression fracture, comprising:
    a superior end plate and an inferior end plate disposed along a vertical axis, the inferior end plate interconnected to the superior end plate such that the superior end plate and the inferior end plate are slidably separable in a vertical direction along the vertical axis;
    the superior end plate further comprising first arm extensions extending downward therefrom and the inferior end plate further comprising second arm extensions extending upward therefrom, the first and second extensions disposed side by side to permit sliding contact therebetween and allow relative vertical movement while preventing substantial lateral displacement in a direction transverse to the vertical axis, wherein the superior end plate comprises a first surface that extends a length greater than a distance between the first arm extensions, and wherein the inferior end plate comprises a second surface that extends a length greater than a distance between the second arm extensions;
    an interior chamber defined by the superior and inferior end plates and the first and second arm extensions, the interior chamber in fluid communication with a port extending from an exterior to the interior chamber;
    wherein the device is deployable within a vertebral body and expandable within the vertebral body by injecting a flowable material into the interior chamber thereby displacing the superior and inferior end plates along the vertical axis, and
    wherein the superior end plate and the inferior end plate comprise planar surfaces for contacting a vertebral body, wherein the planar surfaces each having perforations to permit a flowable material therethrough.

2. The device of claim 1, wherein the flowable material is a liquid.

3. The device of claim 1, wherein the flowable material is selected from one or more of the group consisting of: bone cement, crushed bone, bone pieces, bone matrix, polymers, and microsphere materials.

4. The device of claim 1, wherein the superior and inferior end plates have a lateral width in a direction transverse to the vertical axis and wherein the lateral width is between 4 mm and 6 mm.

5. The device of claim 1, wherein the superior and inferior end plates are arcuate when viewed from the top.

6. The device of claim 1, wherein the superior and inferior end plates have a rectangular shape when viewed from the top.

7. The device of claim 1, wherein the superior and inferior end plates have curvate profiles when viewed from the side.

8. The device of claim 1, wherein the first and second arm extensions are made from a bioresorbable polymer material.

9. The device of claim 1, wherein the superior and inferior end plates are made from a rigid biocompatible metal.

10. The device of claim 1, wherein the superior and inferior end plates and the first and second arm extensions are made from a PEEK material.

11. A device for reducing a vertebral compression fracture, comprising:
    a superior end plate and an inferior end plate disposed along a vertical axis, the inferior end plate slidingly interconnected to the superior end plate such that the superior end plate and the inferior end plate are separable in a vertical direction along the vertical axis;
    a plurality of telescoping vertical segments, each vertical segment comprising a set of first arm extensions extending downward from superior end plate and second arm extensions extending upward from inferior end plate, the first and second arm extensions disposed side by side to permit sliding contact therebetween and allow relative vertical movement and preventing lateral displacement in a direction transverse to the vertical axis, wherein the superior end plate comprises a first surface that extends a length greater than a distance between the first arm extensions, and wherein the inferior end plate comprises a second surface that extends a length greater than a distance between the second arm extensions;
    an interior chamber defined by the superior and inferior end plates and the first and second arm extensions, the chamber in fluid communication with a port extending from an exterior to the interior chamber;
    wherein the device is deployable within a vertebral body and expandable within the vertebral body by injecting a flowable material into the interior chamber thereby displacing the superior and inferior end plates along the vertical axis, and
    wherein the superior end plate and the inferior end plate comprise planar surfaces for contacting a vertebral body, wherein the planar surfaces each having perforations to permit a flowable material therethrough.

* * * * *